United States Patent [19]

Hoelderich et al.

[11] 4,423,273

[45] Dec. 27, 1983

[54] PREPARATION OF OLEFINS FROM METHAOL AND/OR DIMETHYL ETHER

[75] Inventors: Wolfgang Hoelderich; Wolf D. Mross, both of Frankenthal; Matthias Schwarzmann, Limburgerhof, all of Fed. Rep. of Germany

[73] Assignee: BASF Aktiengesellschaft, Fed. Rep. of Germany

[21] Appl. No.: 400,698

[22] Filed: Jul. 22, 1982

[30] Foreign Application Priority Data

Aug. 13, 1981 [DE] Fed. Rep. of Germany ....... 3132024

[51] Int. Cl.³ .............................................. C07C 1/20
[52] U.S. Cl. .................................................... 585/640
[58] Field of Search ......................................... 585/640

[56] References Cited

U.S. PATENT DOCUMENTS

| | | | |
|---|---|---|---|
| 3,702,886 | 11/1972 | Argauer et al. ...................... | 423/328 |
| 3,894,107 | 7/1975 | Butter et al. ......................... | 585/408 |
| 3,979,472 | 9/1976 | Butter .................................. | 585/408 |
| 4,025,576 | 5/1977 | Chang et al. ......................... | 585/322 |
| 4,269,813 | 5/1981 | Klotz .................................... | 423/277 |

*Primary Examiner*—Curtis R. Davis
*Attorney, Agent, or Firm*—Keil & Witherspoon

[57] ABSTRACT

The process for the preparation of olefins by converting methanol and/or dimethyl ether in the presence of a zeolite catalyst is improved by treating the catalyst with hydrogen fluoride. Aluminosilicate zeolites and borosilicate zeolites, especially those of the pentasil type, are chiefly used.

8 Claims, No Drawings

PREPARATION OF OLEFINS FROM METHAOL AND/OR DIMETHYL ETHER

In past years, processes for the preparation of olefins from methanol and/or dimethyl ether have been developed. German Laid-Open Application DOS No. 2,615,150, for example, discloses such a process. The catalyst used is an aluminosilicate zeolite of the ZSM-5 type, which is actually an aromatization catalyst. In the case disclosed, the reaction is steered in the direction of olefin formation by various measures, in particular by shortening the residence time. Other parameters which favor olefin formation are, in particular, the dilution of the methanol and/or dimethyl ether with an inert gas and/or steam and the dilution of the catalyst with a binder. Experience shows that high yields of olefin can be achieved only with very high dilution of the methanol and/or dimethyl ether with an inert gas or steam. The disadvantages of other known processes are the low throughput over the catalyst and its rapid carbonization. There is therefore interest in providing a process in which the catalyst has a long life and the methanol and/or dimethyl ether is converted completely into a hydrocarbon mixture consisting predominantly of $C_2$–$C_4$-olefins.

We have found that a high yield of olefins is obtained by converting methanol and/or dimethyl ether at elevated temperature in the presence of a zeolite catalyst if the catalyst is treated with hydrogen fluoride.

The zeolite catalyst can be used by itself or as a mixture with a binder, such as a silicic acid, magnesium oxide or aluminum phosphate. Aluminum oxides are advantageously used. The pure catalyst can, for example, be pressed to tablets, or it can be mixed with a binder and extruded into a conventional form. From 10 to 90% by weight of binder can be admixed with the catalyst.

The treatment with hydrogen fluoride is preferably carried out directly on the zeolite catalyst before mixing and processing in an extruder. However, it is also possible to subject the finished extruded catalyst to the HF treatment.

In a particular embodiment of the process, the catalyst is pre-treated with HF in the reactor before use, for example by employing hydrogen fluoride diluted with methanol.

The process according to the invention is preferably carried out with an aluminosilicate zeolite or a borosilicate zeolite.

In a preferred embodiment, the zeolite is treated under reflux in from 0.001 N to 1 N HF, preferably from 0.05 to 0.5 N HF, for from 1 to 3 hours before or after being extruded with the binder. The zeolite is filtered off, washed, dried at from 100° to 140° C. and calcined at from 500° to 600° C. Methanol and/or dimethyl ether is converted over this catalyst under a pressure from atmospheric pressure to about 30 bar, preferably under from 0 to 1 bar, and at from 300° to 600° C., preferably from 350° to 500° C. in the case of an aluminosilicate zeolite or from 400° to 550° C. in the case of a borosilicate zeolite. The methanol can contain up to 90% by weight of water.

Other lower alcohols can also be admixed to the methanol. The throughput over the catalyst, expressed in weight per hour space velocity (WHSV)=$h^{-1}$—g of methanol and/or dimethyl ether per g of catalyst and hour is advantageously chosen so that these starting materials are converted almost quantitatively and thus there are no problems with separating off and recycling the dimethyl ether. In general, the WHSV is therefore from 0.5 to 50 $h^{-1}$, preferably from 1 to 10 $h^{-1}$ or from 2 to 15 $h^{-1}$.

A particular advantage of the process according to the invention is that the active time of the catalyst used is increased. For the purposes of the invention, the active time is the period between two regenerations. The overall life of the catalyst is also increased. The effect, according to the invention, of improving the active time manifests itself in particular in reactions at elevated temperatures, for example at from 450° to 500° C. In addition to improving the active time of the catalyst, the treatment with hydrogen fluoride also has the effect of greatly suppressing the undesirable by-product formation of methane and aromatics. Another advantage of the invention is that crude methanol and/or dimethyl ether can be converted into $C_2$–$C_4$-olefins without a diluent.

The Examples which follow illustrate the procedure for the process according to the invention.

EXAMPLE 1

An aluminosilicate zeolite is prepared by hydrothermal synthesis from 65 g of $SiO_2$ (Aerosil 200) and 475 g of $Al(OH)_3$ in 800 g of aqueous hexane-1,6-diamine solution (50:50 mixture) at 150° C. under autogenous pressure in a stirred autoclave. The crystalline product is filtered off, washed, dried at 160° C. for 24 hours and calcined at 500° C. for 24 hours. This aluminosilicate zeolite is composed of 92.6% by weight of $SiO_2$ and 5.6% by weight of $Al_2O_3$.

Two test catalysts A and B are obtained therefrom.

Catalyst A is prepared by extruding the aluminum zeolite with boehmite as a binder in a ratio of 60:40 and drying the extrudate at 110° C. for 16 hours and calcining it at 500° C. for 20 hours.

Catalyst B is prepared by treating 75 g of catalyst A in 200 ml of 0.1 N HF solution under reflux for from 1 to 3 hours. The resulting product is filtered off, washed thoroughly, dried at 110° C. for 16 hours and calcined at 500° C. for 20 hours.

The untreated catalyst (A) and the HF-treated catalyst (B) are then tested on methanol. Table 1 shows the result of converting 25% strength methanol into lower olefins at 400° C. and with a WHSV of 1.4 $h^{-1}$. The end of the active time of the catalyst is indicated by the appearance of dimethyl ether.

TABLE 1

| Catalyst | A | B |
| --- | --- | --- |
| $CH_4$ | 1.7% | 1.4% |
| $C_2H_4$ | 18.0% | 15.7% |
| $C_2H_6$ | 0.3% | 0.3% |
| $C_3H_6$ | 22.5% | 19.8% |
| $C_3H_5$ | 4.7% | 6.0% |
| $C_4H_8$ | 15.5% | 13.6% |
| $C_4H_{10}$ | 11.4% | 14.9% |
| $C_5+$ | 24.0% | 26.4% |
| active time[x] | 26 h | 38 h |
| g of $CH_3OH$/g of catalyst | 36 h | 53 g |

[x]active time = period between two regenerations

The percentages represent the yields, based on the $CH_2$ employed.

Comparison of the Examples shows the improvement in active time caused by treating the catalyst used with hydrogen fluoride.

EXAMPLE 2

A borosilicate zeolite is prepared by hydrothermal synthesis from 64 g of $SiO_2$ (Aerosil 200) and 12.16 g of $H_3BO_3$ in 800 g of aqueous hexane-1,6-diamine solution (50:50 mixture) at 150° C. under autogenous pressure in a stirred autoclave. The crystalline product is filtered off, washed, dried at 160° C. for 24 hours and calcined at 500° C. for 24 hours. This borosilicate zeolite is composed of 88.1% by weight of $SiO_2$ and 3.27% by weight of $B_2O_3$. Two test catalysts A and B are again prepared therefrom.

Catalyst A is prepared by extruding the boron zeolite with boehmite as a binder in a ratio of 60:40 and drying the extrudate at 110° C. for 16 hours and calcining it at 500° C. for 20 hours.

Catalyst B is obtained by treating 75 g of the boron zeolite in 200 ml of 0.1 N HF solution under reflux for from 1 to 3 hours. The resulting product is filtered off, washed thoroughly, dried at 110° C. for 16 hours and calcined at 500° C. for 20 hours. It is then extruded with boehmite as a binder in a ratio of 60:40, and the extrudate is again dried at 110° C. for 16 hours and calcined at 500° C. for 20 hours.

Table 2 which follows shows the results of converting crude methanol into lower olefins on the catalyst forms A and B. In each case, the methanol is converted quantitatively in the reaction.

TABLE 2

| Catalyst | A | B | A | B |
|---|---|---|---|---|
| Temperature | 450° C. | 450° C. | 500° C. | 500° C. |
| WHSV | 7.8 hours$^{-1}$ | 7.8 hours$^{-1}$ | 7.8 hours$^{-1}$ | 7.8 hours$^{-1}$ |
| $CH_4$ | 2.7% | 0.6% | 9.3% | 1.9% |
| $C_2H_4$ | 6.2% | 4.1% | 9.2% | 7.2% |
| $C_2H_6$ | 0.2% | 0.1% | 0.8% | 0.2% |
| $C_3H_6$ | 35.2% | 30.2% | 39.7% | 33.7% |
| $C_3H_8$ | 2.0% | 0.9% | 1.6% | 1.2% |
| $C_4H_8$ | 18.8% | 17.3% | 19.5% | 18.3% |
| $C_4H_{10}$ | 4.1% | 3.8% | 1.8% | 1.5% |
| $C_5+$ | 27.5% | 39.3% | 15.7% | 30.8% |
| active time$^x$ | 45 hours | 79 hours | 11 hours | 48 hours |
| g of $CH_3OH$/ g of catalyst | 390 g | 616 g | 86 g | 374 g |

$^x$Active time = period between two regenerations

The percentages represent the yields, based on the $CH_2$ employed.

The results of the comparative experiments show the improvement in active time effected by the hydrogen fluoride treatment according to the invention on the borosilicate catalyst used. This advantageous effect is particularly marked at elevated temperatures. It is also clear that the formation of methane is substantially suppressed at the high temperature of 500° C.

We claim:

1. A process for the preparation of olefins by converting methanol and/or dimethyl ether at elevated temperature in the presence of a zeolite catalyst which has been treated by contacting the zeolite with hydrogen fluoride.

2. A process as set forth in claim 1, wherein an aluminosilicate zeolite is used as the catalyst.

3. A process as set forth in claim 1, wherein a borosilicate zeolite is used as the catalyst.

4. A process for the preparation of olefins by converting methanol and/or dimethyl ether at elevated temperature in the presence of a pentasil zeolite catalyst, which catalyst has been treated by contacting the pentasil zeolite with a 0.001 N-1 N solution of hydrogen fluoride.

5. A process as set forth in claim 4, wherein the catalyst is pre-treated with hydrogen fluoride in the reactor before use.

6. A process as set forth in claim 5, wherein the treatment is carried out with a methanolic solution.

7. A process for the preparation of olefins by converting methanol and/or dimethyl ether at from 350° to 500° C. and under a pressure from atmospheric pressure to 30 bar in the presence of an aluminosilicate zeolite of the pentasil type which has been pre-treated with hydrogen fluoride.

8. A process for the preparation of olefins by converting methanol and/or dimethyl ether at from 400° to 500° C. and under a pressure from atmospheric pressure to 30 bar in the presence of a borosilicate zeolite of the pentasil type which has been pre-treated with hydrogen fluoride.

* * * * *